US007627551B2

(12) United States Patent
Morgan

(10) Patent No.: US 7,627,551 B2
(45) Date of Patent: Dec. 1, 2009

(54) RETRIEVING CASE-BASED REASONING INFORMATION FROM ARCHIVE RECORDS

(75) Inventor: Alexander P. Morgan, Birmingham, MI (US)

(73) Assignee: GM Global Technology Operations, Inc., Detroit, MI (US)

( * ) Notice: Subject to any disclaimer, the term of this patent is extended or adjusted under 35 U.S.C. 154(b) by 290 days.

(21) Appl. No.: 11/625,998

(22) Filed: Jan. 23, 2007

(65) Prior Publication Data

US 2008/0177702 A1    Jul. 24, 2008

(51) Int. Cl.
*G06F 7/00* (2006.01)
(52) U.S. Cl. .......................................... 707/2
(58) Field of Classification Search ........... 707/2
See application file for complete search history.

(56) References Cited

U.S. PATENT DOCUMENTS 5,224,206 A * 6/1993 Simoudis ..................... 706/61
5,715,374 A * 2/1998 Heckerman et al. ........... 706/46
7,136,852 B1 * 11/2006 Sterling et al. ................ 707/5
2004/0044542 A1 * 3/2004 Beniaminy et al. ............ 705/1
2005/0137832 A1 * 6/2005 Yemini et al. ................ 702/183

* cited by examiner

Primary Examiner—Charles Rones
Assistant Examiner—Fazlul Quader

(57) ABSTRACT

A computer implemented method for using case-based reasoning (CBR) information retrieval processes is provided. The method includes: accessing a data model including symptom attributes and solution attributes; receiving a query from a requestor specifying one or more values for one or more of the symptom attributes; executing the query including searching a database of archive records that are not structured to facilitate CBR for the specified symptom attribute values and receiving a subset of the archive records that include the specified values; determining values associated with one or more of the solution attributes for each of the records in the subset; and creating a temporary case record for each of the records in the subset, each of the temporary case records comprising a pointer to the corresponding record in the subset and a heading section including the symptom attributes, the specified symptom attribute values, the solution attributes, and the solution attribute values associated with the corresponding record in the subset, thereby creating a temporary case base from archive records in real time in response to the values specified in the query.

20 Claims, 2 Drawing Sheets

RETRIEVING CASE-BASED REASONING INFORMATION FROM ARCHIVE RECORDS

BACKGROUND OF THE INVENTION

The present disclosure relates generally to case-based reasoning (CBR), and in particular, to a method of using archive data to retrieve case-based information.

CBR attempts to model human reasoning by recalling previous experiences and adapting them to a current situation. In CBR, the primary knowledge source is a memory of stored cases recording prior specific episodes, or issues. A common application of CBR is in diagnostic systems. The notion is that similar prior issues are a useful starting point for solving new issues. Thus, the success of a CBR knowledge system will depend on both the case base (stored memory) as well as the system's ability to recognize and retrieve past cases that will be helpful to the current issue. Typically, a case is produced after an issue is solved and includes a description of the symptoms (e.g., fault codes, data plots, visual inspections), a description of the root cause of the issue and a resolution of the issue (e.g., repairs). In addition to structured case records, there may be useful diagnostic information stored in archive records that have not been converted into structured case records. Archive records may not have been converted for a variety of reasons such as cost to convert when compared to the expected number of accesses to the records.

A company that provides diagnostic services may store a large volume of archive records containing data describing solutions, or "solved problems." For example, call centers usually have a mechanism for logging calls with some kind of summary of problem and proposed solutions. Warranty databases generally keep records of labor operations for products under warranty. Medical insurance systems similarly keep a record of each billable medical expense. From such archives and databases it is possible to extract problems and solutions, to create a case base for a diagnostic CBR. In practice, however, this historical data (archives) is difficult to use and implement in an efficient manner. The archives often contain "dirty," incomplete, inconsistent, and/or out-of-date data. In addition, the archive data may include unstructured data. These and other issues require a resolution before the case base is created.

A data record is "dirty" if the data record is defective in some way. In particular, a dirty data record may have fields that are blank, that should be filled in, or has fields that are filled in with incorrect data, and/or the format of the data record itself is corrupted in some manner. If the record includes blocks of text, then in certain situations such blocks of text are considered "dirty" if the text is defective in some way, including nonstandard spellings and abbreviations, incorrect grammar, sentence fragments, and any other characteristics that makes the text block difficult to read or process.

The concept of "dirty data" (also referred to herein as "corrupted data") is context and system dependent. Dirty data is capable of being cleaned, repaired, or filtered. Cleaning and repairing, in this context, are essentially synonyms. The two terms refer to filling in blank values, correcting incorrect values and fixing faulty formatting. In short, a correct record replaces the defective record. There are many methods for cleaning data, some requiring little human supervision and others entirely done by a human. With text blocks, for example, the block could be scanned by a spell checker or edited by a human editor or both. However, both of these methods are error-prone and consume a great deal of time to be performed.

Lazy learning is a branch of machine learning that (1) defers processing until there is a request for information, (2) when there is such a request, generates the answer by processing just the stored data needed to generate the answer, and, (3) when the query has been answered, discards the answer instead of saving it. The idea behind lazy learning is to generate knowledge "just in time" from raw data rather than to precompute the knowledge for future use. Lazy learning has emerged from the need to save, or redistribute in time, the computational and storage burdens of machine learning methods.

Many companies maintain large archives of "solved problems" with significant portions of records being stored as text. In an environment where neither time nor resources are constrained, these large archives can be analyzed to create a case base data base following standard CBR methodologies. However, resources are typically constrained. Therefore, solved-problem archives are often abandoned, and new cases are created from new information (e.g., analytical cases might be fabricated by interviewing experts, and/or a new CBR friendly process for capturing cases might be established in the call-center workflow). However, valuable information about how issues were resolved in the past will be lost if the archive records are abandoned. Therefore, there is a need for a process to use the information about past issues (and their symptoms and solutions) without requiring the conversion of all of the archive data records into a CBR format. This process would allow for accessing solutions that have worked in the past, while avoiding the cost of converting a large volume of potentially infrequently accessed archive records into a CBR format.

SUMMARY OF THE INVENTION

Embodiments include a method for using case-based reasoning (CBR) information retrieval processes without creating a case base. A data model including symptom attributes and solution attributes is created. A query is received from a requestor specifying one or more values for one or more of the symptom attributes. The query is executed and execution includes searching a database of archive records for the specified symptom attribute values and receiving a subset of the archive records that include the specified values. Values associated with one or more of the solution attributes for each of the records in the subset are determined. A temporary case record is created for each of the records in the subset. Each of the temporary case records include a pointer to the corresponding record in the subset and a heading section that includes: the symptom attributes, the specified symptom attribute values, the solution attributes, and the solution attribute values associated with the corresponding record in the subset. In this manner, a temporary case base is created from archive records in real time in response to the values specified in the query.

Other embodiments include a system for using CBR information retrieval processes without creating a case base. The system includes a data model, a database and a processor. The data model is in communication with a network and includes symptom attributes and solution attributes. The archive record database includes archive records and is in communication with the network. The processor is in communication with the data model and the database via the network and includes computer instructions for facilitating a method. The method includes receiving a query from a requestor specifying one or more values for one or more of the symptom attributes. The query is executed and execution includes searching the database of archive records for the specified symptom attribute values and receiving a subset of the archive records that include the specified values. Values associated with one or more of the solution attributes for each of the records in the subset are determined. A temporary case record is created for each of the records in the subset. Each of the temporary case records include a pointer to the corresponding record in the subset and a heading section that includes: the symptom attributes, the specified symptom attribute values, the solution attributes, and the solution attribute values associated with the corresponding record in the subset. In this manner, a temporary case base is created from archive records in real time in response to the values specified in the query.

In a further aspect, a computer program product for using CBR information retrieval processes without creating a case base comprises a storage medium readable by a processing circuit and storing instructions for execution by the processing circuit for performing a method. The method includes creating a data model that includes symptom attributes and solution attributes. A query is received from a requester specifying one or more values for one or more of the symptom attributes. The query is executed and execution includes searching a database of archive records for the specified symptom attribute values and receiving a subset of the archive records that include the specified values. Values associated with one or more of the solution attributes for each of the records in the subset are determined. A temporary case record is created for each of the records in the subset Each of the temporary case records include a pointer to the corresponding record in the subset and a heading section that includes: the symptom attributes, the specified symptom attribute values, the solution attributes, and the solution attribute values associated with the corresponding record in the subset. In this manner, a temporary case base is created from archive records in real time in response to the values specified in the query.

BRIEF DESCRIPTION OF THE DRAWINGS

Referring to the exemplary drawings wherein like elements are numbered alike in the several FIGURES.

DETAILED DESCRIPTION OF EXEMPLARY EMBODIMENTS

Figure 1:
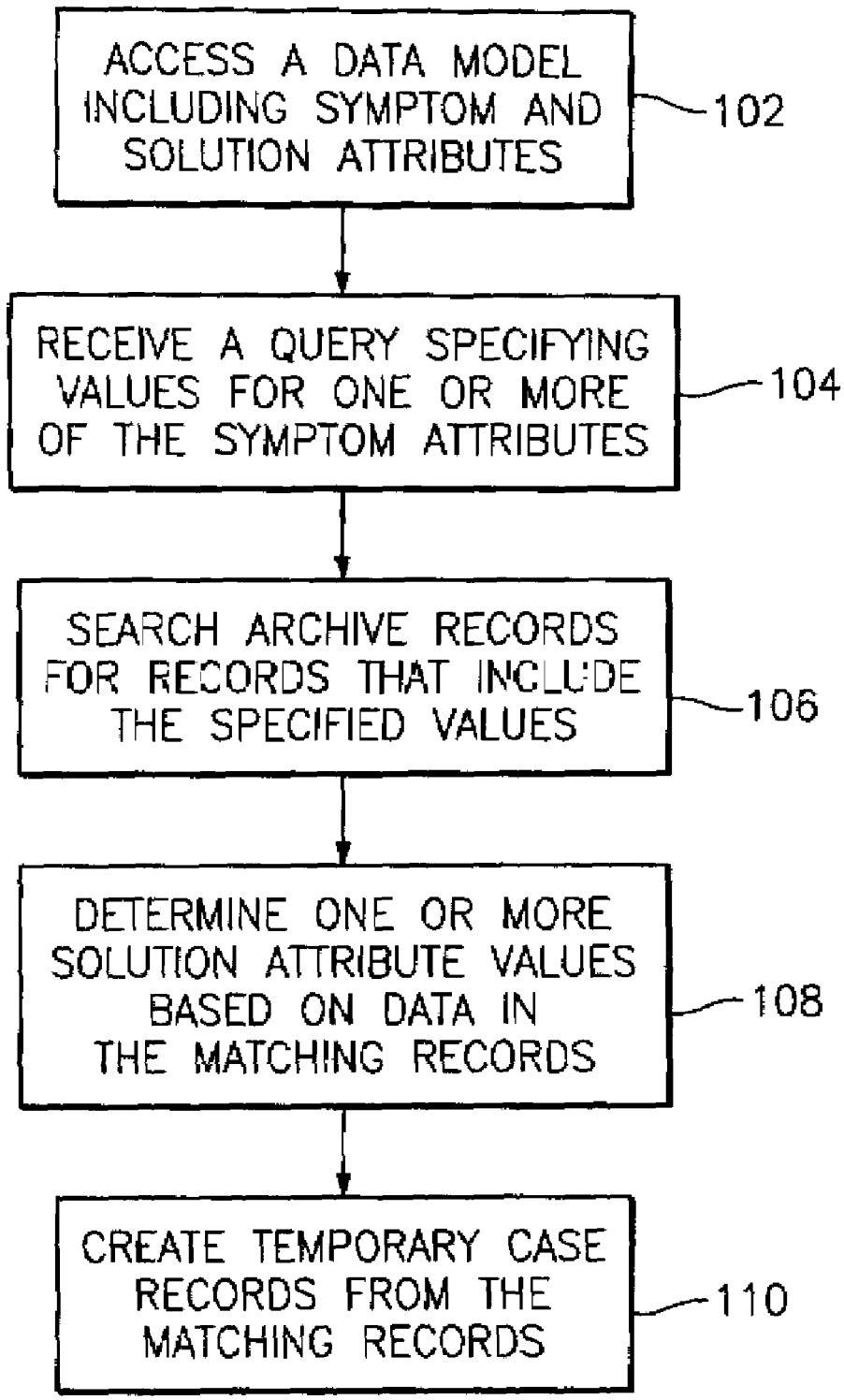
FIG. 1 depicts a process flow that may be implemented by exemplary embodiments to utilize CBR information retrieval processes without creating a case base.

Exemplary embodiments utilize archive records to achieve case-based reasoning (CBR) information retrieval without creating a case base. A query triggers a search of the archive records and archive records relevant to that query alone are utilized to assemble a local, or temporary case base. In exemplary embodiments, information extraction (IE) tools are utilized to identify and select the archive records that match the query. The local, or temporary, case base is deleted when the query requestor exits the query or when the query requestor exits the query software program.

In exemplary embodiments, a "lazy learning" approach is taken, in that the query triggers a real time search of the archive records and that the results of the search are not permanently stored. In response to the query, records relevant to that query alone are used to assemble a "best answer" from the archive records. Exemplary embodiments are more robust and efficient than creating a permanent case base from the archive records. Exemplary embodiments differ from typical database querying because portions of the case base are being created in real time using IE tools. IE may be performed using commercially available tools such as BBN's Identifinder and The University of Sheffield's ANNIE.

An exemplary embodiment described herein relates to archive records that contain call-center logs. It is assumed that the call-center log under consideration has not been structured to facilitate CBR. The main purpose of the call-center log is to document a number of calls and to allow operators to reference pertinent details from previous calls. It is assumed that the call-center logs include a number of named attributes and a number of blocks of "free text." The named attributes are filled-in automatically or via pull-down menus, or they may simply be filled in with words or phrases at a user's discretion. Such attributes might include a date of a call, a name of the operator, some context classification attributes (e.g., what defective appliance is being diagnosed), and perhaps a category of problem type (e.g., a list of symptom categories or a list of repair categories). The free text may be used to capture specific details of the problem, or symptoms, in the caller's own words and also the operator's interpretation of the problem, along with suggestions for solutions, or repairs.

Of particular interest are archives authored by domain experts rather than operators with little domain knowledge. When authors are domain experts, it is natural that they be allowed considerable latitude of expression. In this sort of archive, a record is essentially a note from a person for a small group of peers to record what happened a short time ago, in a context that they all fully understand. Casual mistakes and incompleteness are commonplace in such circumstances, and disciplined data entry is not commonplace. The result is that the free text contains idiosyncratic wordings of the problem descriptions and proposed solutions. In fact, in one call-center archive, twenty-five different spellings of the word "intermittent," including abbreviations, were discovered.

In the simplest manifestation of classic CBR, the case consists entirely of named attributes. A query is a choice of attribute values describing the symptoms, or problem. A response to the query is a set of cases similar to the query. Similarity between cases is defined by first defining similarity for each attribute. For every pair of values the attribute is instantiated by, a similarity is assigned. This similarity is represented numerically by a number located in a region between 0.0 (not at all similar) to 1.0 (essentially identical). Then, the case-to-case similarity is defined as a weighted sum of the attribute similarities.

In exemplary embodiments described herein, the archive records do not consist entirely of named attributes. In particular, some of the named attributes do not have a standard set of values, and some, or all, of the basic information in the archive records is in free-text blocks. Further, it is also commonplace to have hundreds of thousands of records and that a certain percentage of such data be dirty, or corrupted. Having named attributes without a standard set of values can lead to corrupted data, while having free-text blocks impacts the ability to extract key information from the text. IE considers methods for extracting knowledge from text. It is closely related to text mining, but it has a somewhat different emphasis. Mining activities attempt to discover a few interesting records out of a large set of records. IE functions to summarize the free-text blocks in each record by extracting key concepts into a predefined template, in essence creating new structured entities for each record. It is possible that IE would be an intermediate step in a text mining system, but not necessarily. The lazy case creation method utilized by exemplary embodiments is designed to minimize the cost of IE tools in satisfying a query. Note that the IE tools may also be required to address the first issue of having named attributes without a standard set of values. In this case, the IE tools may be utilized to determine which of a set of standard values my be inferred from the data.

The field of IE is emerging with more and more powerful and effective tools, but it is still expensive and generally requires human supervision and validation. For example, coming back to the call-center log illustration, in one call-center archive, one of the authors consistently entered text with no capital letters and no punctuation. These "run on" blocks of text are difficult to read, even by humans. The challenge of parsing without clear grammatical cues is at a greater level of difficulty than parsing well-punctuated text.

In general, a first step with any archive is to filter and clean the records by whatever means are feasible. Some or all of the incomplete or inconsistent records may be eliminated from further consideration. In addition, some or all of the incomplete or inconsistent records may be repaired. This processing is known in the art and may be performed utilizing commercially available tools such as HelpIT Intelligent Data Cleansing, IBM DataJoiner, and SAS Data Quality—Cleanse. In exemplary embodiments, it is assumed that incomplete or inconsistent records have been eliminated or repaired before retrieving the CBR information from the archive records.

Referring to the call-center log example, the fundamental information required by a case record includes symptoms (also referred to herein as "problems") and repairs (also referred to herein as "solutions"). Symptoms pertain to a defective object with a description of a problem with it (e.g., the network connection doesn't work; the refrigerator doesn't cool). Repairs pertain to actions performed on defective objects (e.g., the network card is replaced; the refrigeration coil is repaired and refilled with refrigerant gas). This information does not come "for free" in the kind of archive records utilized by exemplary embodiments. The information is deduced or extracted by using the IE tools described above.

FIG. 1 depicts a process flow that may be implemented by exemplary embodiments to utilize CBR information retrieval processes without creating a case base. The processing depicted in FIG. 1 creates a temporary case base in real time from archive records based on attribute values specified in a query. At block 102, a data model including symptom attributes and repair attributes is accessed. Alternatively, the data model may not already exist and may be created by exemplary embodiments.

Example symptom attributes for a vehicle call-center include: main symptom group, for specifying a high level classification of the symptoms (e.g., air leak, noise, odor, etc.); symptom group, for specifying more information about the symptom (e.g., engine has burning odor, air bag indicator is on, etc.); symptom, for specifying the customer complaint (e.g., noise); symptom detail, for specifying details about the symptom (e.g., rattling noise); functional component/system, for specifying which part of the product is exhibiting the symptom; frequency for specifying how often the symptom is observed or experienced; environment condition, for specifying condition of the environment when the symptom occurs (e.g. raining, 95 degrees F., etc.); and vehicle condition, for specifying operating conditions of the vehicle when the symptom occurs (e.g., just after starting, under load, etc.).

Example solution attributes for a vehicle call-center include: action taken, for specifying the repair action taken; component name; component location, for specifying the location of the component acted upon; labor operation codes; and additional action comments for specifying additional solution information as free-form text.

The above symptom and solution attributes are intended to be example attributes and additional attributes may be implemented along with all or a subset of the example attributes. In exemplary embodiments all of the values associated with each of the symptom and solution attributes are known. In alternate exemplary embodiments all of the values associated with each of the symptom and solution attributes are not known.

At block 104, a query specifying a value(s) for one or more of the symptom attributes is received from a requester. In exemplary embodiments, an user interface screen listing each of the symptom attributes is utilized by requesters when creating the query. In addition, when all of the values of a symptom attribute are known, a pull down selection box (reflecting symptom attributes in the data model) may be presented to the requestor to create the query. Further, when some of the values of a symptom attribute are known, the requestor may select a known value or may be prompted to enter a value. The requestor may specify values for one or more of the symptom attributes. In addition, the requester may specify more than one value for a single symptom attribute.

At block 106, the query is executed by searching a database of archive records (e.g., call center logs) for archive records that include the specified symptom values. In exemplary embodiments, where the archive records include one or more formatted attribute fields, some of the symptom attributes will be known without performing an IE process. In this case, those archive records that do not satisfy the query for the formatted attribute fields will be eliminated from further consideration. IE is then performed on the remaining archive records to determine if the attribute fields corresponding to non-formatted data (e.g., free-form text) in the archive records contain the symptom attribute values specified in the query. In exemplary embodiments, the match does not have to be exact and the IE tool searches for variations in spelling, abbreviations, etc. of the specified values. The state of the art in natural-language computation offers a considerable degree of sophistication in determining syntactically related words, via the process of "stemming." In exemplary embodiments, the IE process is performed one attribute at a time and the pool of possibly relevant archive records will shrink in size as each attribute is populated with a value. Thus, as each symptom attribute related to each archive record is populated with a value, the archive records that do not match the query are eliminated from further consideration. The result of this process is a subset of the archive records with associated populated symptom attribute values that match the symptom attribute values specified in the query.

One reason for organizing the IE in this manner is to limit the amount of resources required. The choice of the sequence of symptom attribute values to determine may follow a maximum entropy logic or some other scheme to improve efficiency. In essence, exemplary embodiments perform a guided search for symptom attribute values where the IE machinery rather than a human is providing the specified values.

At block 108, each of the archive records in the subset determined at block 106 is analyzed to extract any solution attribute values that are associated with the one or more solution attributes. In exemplary embodiments, IE is utilized to populate the solution attributes. In exemplary embodiments, values defined in the data model and associated with each of the solution attributes (and variations including misspellings and abbreviations) are searched for and extracted from each of the archive records in the subset. None, one or a plurality of values may be identified for each of the solution attributes.

In exemplary embodiments, temporary case records are created for each of the archive records in the subset. Each of the temporary case records includes a pointer to its corresponding archive record and a heading section. The heading section includes the symptom attributes along with the value(s) specified by the query for one or more of the symptom attributes and the solution attributes along with the value(s) located in the archive record for one or more of the solution attributes. The temporary case records may be grouped by those that have the same repair attribute values and ordered from largest to smallest groups. These groups containing temporary case records are returned to the requestor at block 110 in response to the query, with the largest group representing the most frequent solutions for the symptoms specified by the query. If the values in the solution attributes do not provide enough information, then the associated archive record can be examined to get more details.

In exemplary embodiments, once the requester has exited the query, or once the requestor has exited the query software, the temporary case records associated with the query are deleted. In alternate exemplary embodiments, the temporary case records may be flagged to be added to an existing call center case base.

In exemplary embodiments, a call center case base of symptoms and solutions is also accessed in response to the query. Typical CBR techniques are utilized to identify cases that satisfy the query. In exemplary embodiments, the same data model is defined for both the archive records and the case base records. In this exemplary embodiment, the identified cases and the temporary case records are both returned to the requester. The identified cases and the temporary case records may be sorted before being transmitted to the requestor as described in reference to the temporary case records.

In further exemplary embodiments, the subset of records in the archive records that include the values specified in the query are marked or recorded as being applicable to a current query. By denoting archive records that have been accessed, management of the archive records can be performed. For example, archive records that have not been accessed (i.e., not in the subset of archive records that include the values specified by a query) within a specified period of time (e.g., one year, two years, five years) may be permanently deleted from the archive records. In another example, archive records that have been accessed a specified number to times (one, five, ten) may be added to the call center case base database.

Exemplary embodiments may be utilized for applications other than call-center operations. For example, CBR has been applied to classification tasks, such as to determine the type of an organism from observed attributes. CBR has also been applied to design tasks, such as an optimal layout of items. As described herein, a major application of CBR is in helpdesks. Specifically, a helpdesk operator enters a client's description of the client's problem/symptom (or case) into the CBR system. Exemplary embodiments described herein focus on archive records that relate to a call-center log. However, the exemplary embodiments are not limited in any way to only such a system. One skilled in the art may adapt the exemplary embodiments to various different systems without departing from the scope of this invention.

Figure 2:
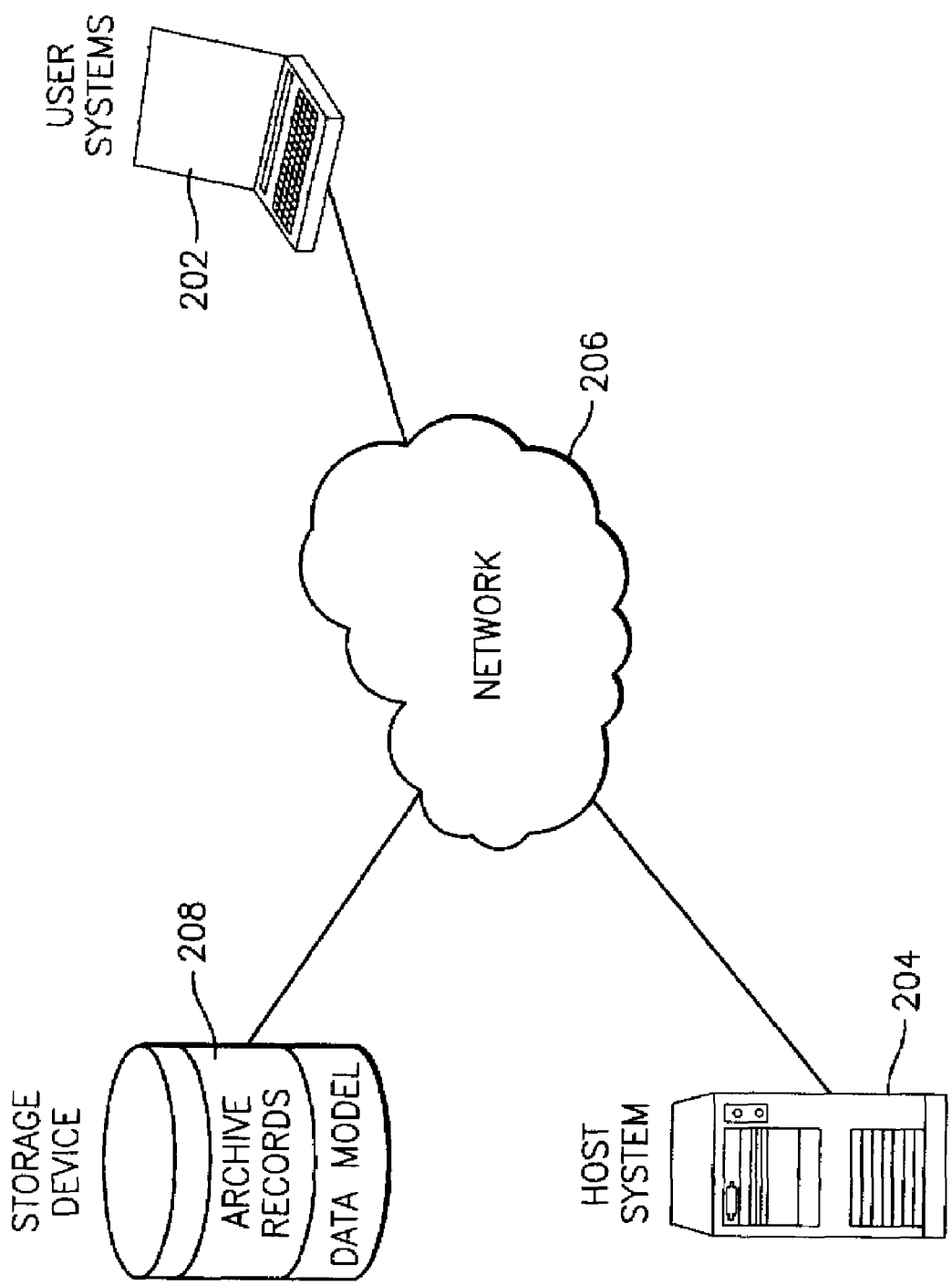
FIG. 2 is a block diagram of an exemplary system that may be implemented by exemplary embodiments to utilized CBR information retrieval processes without creating a case base.

FIG. 2 is a block diagram of an exemplary system that may be implemented by exemplary embodiments to utilized CBR information retrieval processes without creating a case base. The system includes one or more user systems 202 through which requesters at one or more geographic locations contact the host system 204. The host system 204 includes a processor to execute instructions for facilitating the information retrieval processes described herein. This includes instructions (e.g., a commercial software tool) to execute the IE tasks described herein. The user systems 202 are coupled to the host system 204 via a network 206. Each user system 202 is implemented using a general-purpose computer executing a computer program for carrying out the processes described herein. The user systems 202 may be personal computers (e.g., a lap top, a personal digital assistant) or host attached terminals. If the user systems 202 are personal computers, the processing described herein is shared by a user system 202 and the host system 204 (e.g., by providing an applet to the user system 202).

The network 206 may be any type of known network including, but not limited to, a wide area network (WAN), a local area network (LAN), a global network (e.g., Internet), a virtual private network (VPN), and an intranet. The network 206 may be implemented using a wireless network or any kind of physical network implementation known in the art. A user system 202 may be coupled to the host system through multiple networks (e.g., intranet and Internet) so that not all user systems 202 are coupled to the host system 204 through the same network. One or more of the user systems 202 and the host system 204 may be connected to the network 206 in a wireless fashion. In one embodiment, the network is the Internet and one or more user systems 202 execute a user interface application (e.g. a web browser) to contact the host system 204 through the network 206 while another user system 202 is directly connected to the host system 204. In another exemplary embodiment, the user system 202 is connected directly (i.e., not through the network 206) to the host system 204 and the host system 204 is connected directly to or contains the storage device 208. In another exemplary embodiment, the user system 202 includes a stand-alone application program to perform the processing described herein.

The storage device 208 is implemented using a variety of devices for storing electronic information. It is understood that the storage device 108 may be implemented using memory contained in the host system 204 or it may be a separate physical device. The storage device 208 is logically addressable as a consolidated data source across a distributed environment that includes a network 206. Information stored in the storage device 208 is retrieved and manipulated via the host system 204 or directly via the user systems 202. The storage device 208 includes the data model and the archive records and, optionally, a case base database corresponding to the data model. The storage device 208 may also include other kinds of data such as information concerning the updating of the data model and IE related data.

The host system 204 depicted in FIG. 2 is implemented using one or more servers operating in response to a computer program stored in a storage medium accessible by the server. The host system 204 operates as a network server (e.g., a web server) to communicate with the user system 202. The host system 204 handles sending and receiving information to and from the user system 202 and can perform associated tasks. The host system 204 may also include a firewall to prevent unauthorized access to the host system 204 and enforce any limitations on authorized access. For instance, an administrator may have access to the entire system and have authority to modify portions of the system. A firewall may be implemented using conventional hardware and/or software as is known in the art.

The host system 204 may also operate as an application server. The host system 204 executes one or more computer programs to perform the processing described herein. Processing may be shared by the user system 202 and the host system 204 by providing an application (e.g., java applet) to the user system 202. Alternatively, the user system 202 can include a stand-alone software application for performing a portion or all of the processing described herein. As previously described, it is understood that separate servers may be utilized to implement the network server functions and the application server functions. Alternatively, the network server, the firewall, and the application server may be implemented by a single server executing computer programs to perform the requisite functions.

Exemplary embodiments have several advantages, or technical effects, over previous efforts to convert the whole archive data base to a case base at one time. One advantage is that the IE process requires large amounts of computational resources and is prone to error. Thus, the IE process often requires human supervision. By making the set of archive records smaller on which IE process must be performed, the amount of computer resources and human time required is reduced. At the very least, the requirement for these resources is spread out in time, and this is generally preferred, especially for human resources. The advantage is increased if many of the symptom attributes are given with the original records. In the worst case where there are no named attributes or structured fields in the archive records (i.e., each archive record is simply a block of text), the IE process described herein would still save resources because it is organized in a sequence of passes, first, to generate the symptom attribute values and then the solution, or repair attribute values, just as described above.

An additional benefit occurs when the archive is constantly being added to because the lazy approach described herein generates more up-to-date information. Ordering solutions by frequency-of-occurrence provides a natural form of validation and provides "most likely solution" information when the symptoms do not generate just one solution. As a form of "automatic validation," the repairs with just a few associated records are ignored. The possibility of missing valid solutions that appear only in low frequencies would occur only as a symptom/problem type is first emerging or where the same symptom/problem-solution is "written up" in very different ways. These situations are difficult to handle by any method, especially in environments where the data may be corrupted.

A further benefit is that archive records that do not correspond to any queries are not processed. This occurs with out-of-date records or faulty records. These records are not identified explicitly. In fact, the records are simply not accessed. Over time, however, records that are not accessed are removed from the archive, thus creating a clean database, and accurate matches of the current case entered by the user and the portion of the previous cases. The CBR system is forced to search in a more limited or narrow database, thus decreasing computational processing time.

As described above, embodiments may be in the form of computer-implemented processes and apparatuses for practicing those processes. In exemplary embodiments, the invention is embodied in computer program code executed by one or more network elements. Embodiments include computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Embodiments include computer program code, for example, whether stored in a storage medium, loaded into and/or executed by a computer, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying out this invention, but that the invention will include all embodiments falling within the scope of the claims.

What is claimed is:

1. A computer implemented method for using case-based reasoning (CBR) information retrieval processes, the method comprising:
    accessing a data model including symptom attributes and solution attributes;
    receiving a query from a requestor specifying one or more values for one or more of the symptom attributes;
    executing the query including searching a database of archive records that are not structurted to facilitate CBR for the specified symptom attribute values and receiving a subset of the archive records that include the specified values;
    determining values associated with one or more of the solution attributes for each of the records in the subset; and
    creating a temporary case record for each of the records in the subset, each of the temporary case records comprising a pointer to the corresponding record in the subset and a heading section including the symptom attributes, the specified symptom attribute values, the solution attributes, and the solution attribute values associated with the corresponding record in the subset, creating a temporary case base from archive records in real time in response to the values specified in the query.

2. The method of claim 1 further comprising transmitting the temporary case records to the requester.

3. The method of claim 2 further comprising deleting the temporary case records after performing the transmitting.

4. The method of claim 1 further comprising:
    identifying cases in a case base database that include the specified symptom attribute values; and
    transmitting the identified cases and the temporary case records to the requestor.

5. The method of claim 4 further comprising deleting the temporary case records after performing the transmitting.

6. The method of claim 4 further comprising ordering the identified cases and the temporary case records from largest number of solution attribute values to smallest number of solution attribute values before performing the transmitting.

7. The method of claim 1 wherein the searching the database of archive records includes searching free form text for the specified symptom attribute values.

8. The method of claim 1 wherein the determining values includes processing free form text to locate the solution attributes.

9. The method of claim 1 wherein the executing the query further includes recording an access to the archive records in the subset and the method further comprises permanently deleting archive records that have not been accessed within a specified period of time.

10. The method of claim 1 wherein one or more of the searching the database and the determining values is performed using an information extraction tool.

11. The method of claim 1 wherein one or more of the symptom and solution attributes is associated with a finite set of values.

12. The method of claim 1 wherein all or a subset of the determining is performed using an information extraction tool on unstructured text data contained in the archive records.

13. A computer implemented system for using CBR information retrieval processes, the system comprising:
- a data model in communication with a network and including symptom attributes and solution attributes;
- a database of archive records in communication with the network; and
- a processor in communication with the data model and the database via the network and including computer instructions for facilitating:
  - receiving a query from a requester specifying one or more values for one or more of the symptom attributes;
  - executing the query including searching the database of archive records that are not structured to facilitate CBR for the specified symptom attribute values and receiving a subset of the archive records that include the specified values;
  - determining values associated with one or more of the solution attributes for each of the records in the subset; and
  - creating a temporary case record for each of the records in the subset, each of the temporary case records comprising a pointer to the corresponding record in the subset and a heading section including the symptom attributes, the specified symptom attribute values, the solution attributes, and the solution attribute values associated with the corresponding record in the subset, thereby creating a temporary case base from archive records in real time in response to the values specified in the query.

14. The system of claim 13 wherein the instructions further facilitate transmitting the temporary case records to the requestor.

15. The system of claim 14 wherein the instructions further facilitate deleting the temporary case records after performing the transmitting.

16. The system of claim 14 wherein the instructions further facilitate:
- identifying cases in a case base database that include the specified symptom attribute values; and
- transmitting the identified cases and the temporary case records to the requestor.

17. The system of claim 16 wherein the instructions further facilitate deleting the temporary case records after performing the transmitting.

18. The system of claim 13 wherein the searching the database of archive records includes searching free form text for the specified symptom attribute values.

19. A computer program product for using CBR information retrieval processes, the computer program product comprising:
- a storage medium readable by a processing circuit and storing instructions for execution by the processing circuit for facilitating a method comprising:
  - accessing a data model including symptom attributes and solution attributes;
  - receiving a query from a requestor specifying one or more values for one or more of the symptom attributes;
  - executing the query including searching a database of archive records that are not structured to facilitate CBR for the specified symptom attribute values and receiving a subset of the archive records that include the specified values;
  - determining values associated with one or more of the solution attributes for each of the records in the subset; and
  - creating a temporary case record for each of records in the subset, the temporary case record comprising a pointer to the corresponding record in the subset and a heading section including the symptom attributes, the specified symptom attribute values, the solution attributes, and the solution attribute values associated with the corresponding record in the subset, creating a temporary case base from the archive records in real time in response to the values specified in the query.

20. The computer program product of claim 18 wherein the instructions further facilitate transmitting the temporary case records to the requestor and deleting the temporary case records after performing the transmitting.

* * * * *